(12) United States Patent
Roh et al.

(10) Patent No.: US 11,350,994 B2
(45) Date of Patent: Jun. 7, 2022

(54) SURGERY PLANNING

(71) Applicant: NAVLAB HOLDINGS II, LLC, Seattle, WA (US)

(72) Inventors: Jeffrey Roh, Seattle, WA (US); Justin Esterberg, Mercer Island, WA (US)

(73) Assignee: NAVLAB HOLDINGS II, LLC, Seattle, WA (US)

( * ) Notice: Subject to any disclaimer, the term of this patent is extended or adjusted under 35 U.S.C. 154(b) by 148 days.

(21) Appl. No.: 16/012,464

(22) Filed: Jun. 19, 2018

(65) Prior Publication Data
US 2018/0360543 A1 Dec. 20, 2018

Related U.S. Application Data

(60) Provisional application No. 62/521,537, filed on Jun. 19, 2017, provisional application No. 62/528,480, filed on Jul. 4, 2017.

(51) Int. Cl.
*A61B 34/10* (2016.01)
*G16H 50/20* (2018.01)
(Continued)

(52) U.S. Cl.
CPC ............ *A61B 34/10* (2016.02); *G16H 20/40* (2018.01); *G16H 50/20* (2018.01); *G16H 50/50* (2018.01);
(Continued)

(58) Field of Classification Search
CPC ... A61B 34/10; A61B 34/20; A61B 2034/105; A61B 2034/107; G16H 20/40; G16H 50/50; G16H 50/70; G16H 50/20
(Continued)

(56) References Cited

U.S. PATENT DOCUMENTS

2007/0214013 A1* 9/2007 Silverman .............. G16H 20/40
705/2
2012/0296675 A1* 11/2012 Silverman .............. G16H 50/30
705/3
(Continued)

FOREIGN PATENT DOCUMENTS

AU  2012289973 B2 *  1/2017  ........... A61F 2/3859
CA  2980618 A1 *  9/2016  ............. G06F 17/40

OTHER PUBLICATIONS

Ji, S., Zhao, W., Ford, J. C., Beckwith, J. G., Bolander, R. P., Greenwald, R. M., . . . & McAllister, T. W. (2015). Group-wise evaluation and comparison of white matter fiber strain and maximum principal strain in sports-related concussion. Journal of neurotrauma, 32(7), 441-454. (Year: 2015).*

(Continued)

*Primary Examiner* — Joshua B Blanchette
*Assistant Examiner* — Winston Furtado
(74) *Attorney, Agent, or Firm* — Hamre, Schumann, Mueller & Larson, P.C.

(57) ABSTRACT

Technologies for providing assistance to a surgeon during a surgical procedure are disclosed. An example method includes identifying a medical condition of a patient and recommending surgical procedures for treatment. An optimal surgical procedure is then determined based on correlations between the medical condition of the patient and outcomes of previous surgical procedures for other patients previously suffering from the medical condition. A 3D model of the patient may be created using current images of an affected area of the patient. Successively, a surgeon is trained using a Virtual Reality simulation. During the training, the surgeon may be allowed to provide annotations. Further, the recommended surgical procedures are based on medical data of the patient, including medical images. Surgical paths are retrieved for addressing the surgical need (Continued)

of the patient, and the surgical paths may be overlaid on image segments, for display for the surgeon. A surgical path is selected from the surgical paths, a surgical step belonging to the surgical path is selected, and an image segment selected from the image segments, based on the surgeon's inputs is used to create the surgical plan.

11 Claims, 14 Drawing Sheets

(51) Int. Cl.
*G16H 50/50* (2018.01)
*G16H 50/70* (2018.01)
*A61B 34/20* (2016.01)
*G16H 20/40* (2018.01)

(52) U.S. Cl.
CPC .............. *G16H 50/70* (2018.01); *A61B 34/20* (2016.02); *A61B 2034/105* (2016.02); *A61B 2034/107* (2016.02)

(58) Field of Classification Search
USPC .............................................. 705/2
See application file for complete search history.

(56) References Cited

U.S. PATENT DOCUMENTS

| 2014/0051986 A1* | 2/2014 | Zhao ..................... G06T 7/33 |
| | | 600/424 |
| 2016/0338685 A1* | 11/2016 | Nawana ................ A61B 34/10 |
| 2017/0083666 A1* | 3/2017 | Biancalana ............ G16H 30/20 |
| 2017/0108930 A1* | 4/2017 | Banerjee ................ A61B 90/37 |

OTHER PUBLICATIONS

Card, R., Sawyer, M., Degnan, B., Harder, K., Kemper, J., Marshall, M., . . . & Schuller-Bebus, G. (2014). Perioperative protocol. Inst Clin Syst Improv. (Year: 2014).*

* cited by examiner

SURGERY PLANNING

CROSS-REFERENCE TO RELATED APPLICATION

This Application claims priority from U.S. Provisional Application Nos. 62/521,537, filed Jun. 19, 2017; and 62/528,480, filed Jul. 4, 2017. The disclosures of both applications are hereby incorporated herein by reference in their entireties.

FIELD OF THE DISCLOSURE

Technologies described herein generally relate to creating a plan for surgery utilizing computer assistance, including Artificial Intelligence (AI), which may provide assistance during the surgery.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Each surgical procedure has a different level of associated risk. The risk may arise due to the medical health of the patient before surgery, as well as any errors or shortcomings during surgery. To minimize the risks arising due to a patient's health, a pre-operative evaluation is generally performed. The pre-operative evaluation is performed to identify a patient's history of disease, allergies, and current medical condition. The pre-operative evaluation may include a physical examination, neurological examination, and/or other specialized medical tests. The pre-operative evaluation enables a medical staff to take pro-active steps to reduce risks associated with a forthcoming surgical procedure.

Based on the pre-operative evaluation, a surgeon defines his pre-operative plans and steps for executing a surgical procedure. The pre-operative plans may include a patient's dosage of medication before, during, and after the surgical procedure; surgical devices to be used during the procedure; and a method of handling the surgical devices during the surgical procedure.

A surgeon may also have in mind several machines and methods for operating efficiently on a patient by improving surgical accuracy and minimizing risks during the surgical procedure. Such methods may include storing images of an affected or target area of the patient, storing videos of similar surgical procedures for reference, and training on artificial organs.

During an image-guided surgery, a surgeon makes use of tracked surgical instruments in conjunction with images of a patient, i.e., the surgeon uses images of an ultrasound in order to guide needles being inserted into a liver of a patient for ablation.

Currently, image-guided surgery provides various techniques, such as Three-Dimensional (3D) graphics rendering techniques, medical image shape detection, etc. However, current techniques are prone to inadequate image management. For example, the current techniques require the surgeon to forego performing other activities during the surgical procedure in order to manipulate a view of Computerized Tomography (CT) scans, Magnetic Resonance Imaging (MRI) images, and other visualization medical data, using a mouse-and-monitor interface. Such type of suspension or disruption of the surgical procedure may result in increased time and reduced fluidity.

Further, current techniques for image-guided surgery do not provide a sufficient control and flexibility in viewing the CT scans and the other visualization medical data due to unintuitive and difficult interfaces. For example, 3D viewing systems may display obscured areas of the visualization medical data. Also, the current techniques fail to provide an adequate method to the surgeon for annotating the images during the surgical procedure. But such techniques are difficult, time-consuming, and disruptive.

Further, robotic surgery is a branch of science by which a surgeon uses robots for operating on patients. Such robots improve precision of a surgeon by providing greater control during each stage of a surgical procedure, and thereby reduce chances of errors. Further, several systems provide the surgeons with remote control of robotic arms present in a remote operation theatre by viewing a real-time video display of a surgical area. Based on the video of the patient, the surgeon may remotely control the robotic arms to perform the surgery. Usage of such robots allows the surgeons to minimize entry wounds, reduce blood loss during the surgery, and leave least amount of scarring after the surgery. For example, the Da Vinci® robotic surgical system developed by Imperial College London has been used in general surgical procedures since the early 2000s.

Artificial Intelligence (AI) technologies including machine vision and image analysis complement surgeons' abilities. A few of the already identified uses include highlighting blood vessels, nerve cells, tumor margins, and other important structures that are hard to recognize by naked eye or extrapolation on a screen. Thus, AI may improve a surgeon's analysis of real time visual data of patients, thus improving their surgical procedure.

Augmented Reality (AR) systems are also used by surgeons for overlaying of important information required during a surgical procedure. Such information includes pre-operative images, lab test results, and details of previous such surgical procedure. The information is displayed on multiple monitors stacked around a surgeon in an operation theatre. The information is used by the surgeon while performing the surgical procedure.

Thus, the current state of art merely involves usage of images, lab results, and other historical data related to a patient. All such data is simply projected on a screen for a surgeon's reference.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples. It will be readily understood that the aspects of the present disclosure, as generally described herein, and illustrated in the figures, can be arranged, substituted, combined, separated, and designed in a wide variety of different configurations, all of which are explicitly contemplated herein.

Figure 1A:
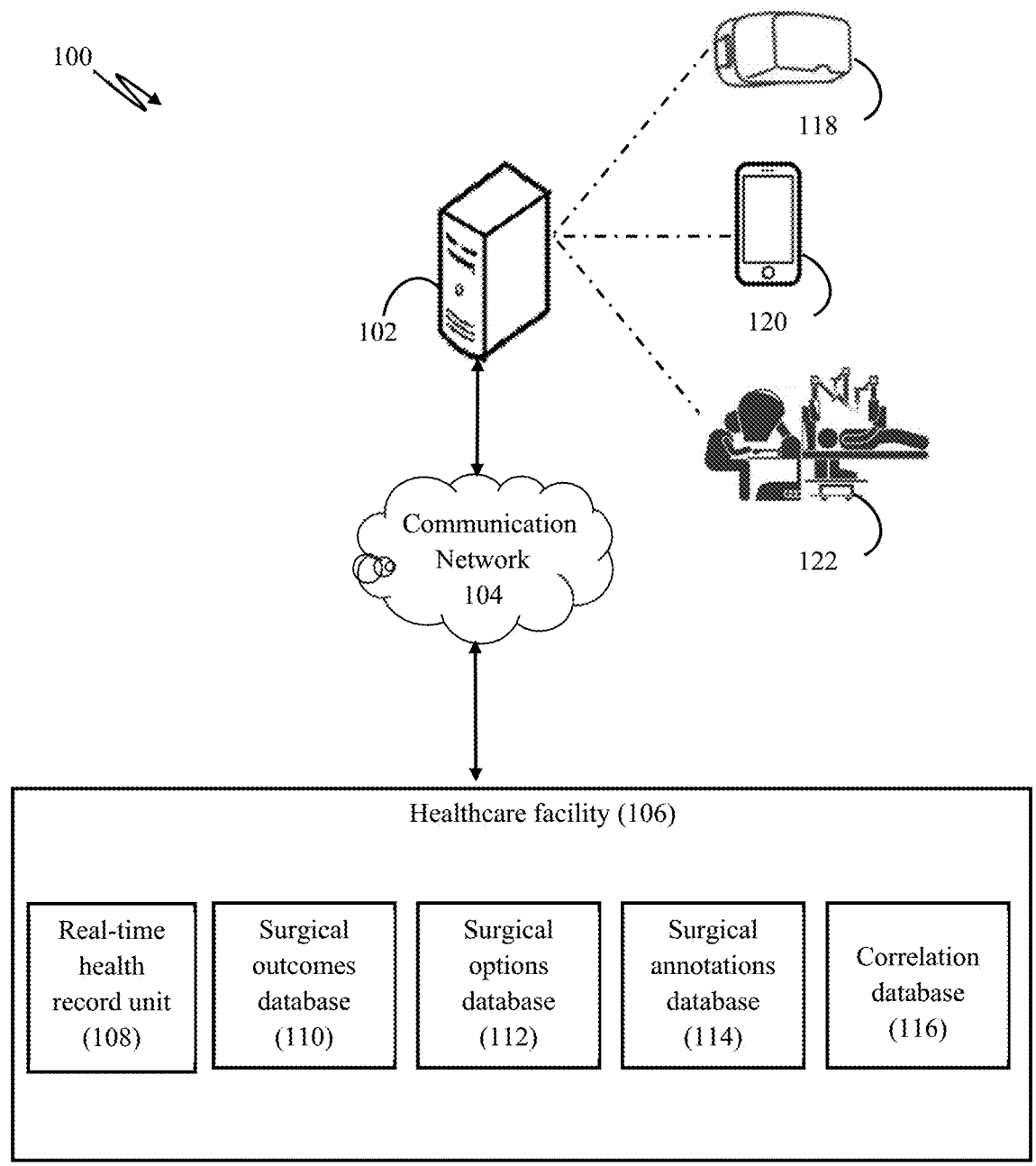
FIG. 1A illustrates a network connection diagram 100 of a system 102 for providing surgical assistance during a surgical procedure, according to an embodiment.

FIG. 1A illustrates network connection diagram 100 of a system 102 for providing surgical assistance during a surgical procedure, according to an embodiment. The system 102 may be connected to a communication network 104. The communication network 104 may further be connected with a healthcare facility 106 for facilitating data transfer between the system 102 and the healthcare facility 106.

The communication network 104 may be a wired and/or a wireless network. The communication network 104, if wireless, may be implemented using communication techniques such as Visible Light Communication (VLC), Worldwide Interoperability for Microwave Access (WiMAX), Long Term Evolution (LTE), Wireless Local Area Network (WLAN), Infrared (IR) communication, Public Switched Telephone Network (PSTN), Radio waves, and other communication techniques known in the art.

The healthcare facility 106 may comprise a real-time health record unit 108 and a group of databases for storing different information required during a surgical procedure. The group of databases may comprise a surgical outcomes database 110, surgical options database 112, surgical annotations database 114, and a correlation database 116. Different databases are used in present case; however, a single database may also be used for storing the data. Usage of the different databases may also allow segregated storage of different data and may thus reduce time to access required data.

In one embodiment, the surgical outcomes database 110 may be configured to store results of previous surgeries for several patients. The results may be stored in a structured manner. In one case, the results may be organized based on types of surgical procedures, followed by patients' medical histories, followed by pre-plan of surgical procedures, and before and after annotations of surgeons for the surgical procedures.

The surgical outcomes database 110 may further store images of the patients. The images may be any of camera images, Magnetic Resonance Imaging (MRI) images, and X-Ray images. The surgical outcomes database 110 may also comprise actual VR training data used by a surgeon, for pre-planning of a surgical procedure. The surgical outcomes database 110 may also include data by a Three-Dimensional (3D) camera during the actual surgical procedure and all related monitor data, which is displayed on a screen during the surgical procedure. The surgical outcomes database 110 may also include unexpected or adverse events occurring in a time-sequence of pre-plan and actual results. The surgical outcomes database 110 may also include annotations provided by previous surgeons.

In at least one embodiment, the surgical options database 112 may be implemented as a query on the surgical outcomes database 110. The surgical options database 112 may comprise data organized in a surgical options structure. In at least one scenario facilitated by the embodiment, for a particular surgical procedure performed on a particular type of patient, the surgical options database 112 may store information related to each event step, such as details of the events that went well, occurrence of adverse events, frequency of the adverse events, annotations made by a surgeon, and usefulness of the annotations.

In at least one embodiment, the surgical annotations database 114 may be implemented as a query on the surgical outcomes database 110. The surgical annotations database 114 may extract a surgeon's annotations from the surgical outcomes database 110 and may organize the surgeon's annotations. The surgical annotations database 114 may also input a current surgeon's annotations, made either during training and preplanning or during an actual surgical procedure by the current surgeon.

In at least one embodiment, the correlation database 116 may be implemented as a real-time query of all databases (surgical outcomes database 110, surgical options database 112, and surgical annotations database 114) to find correlations based upon a current surgical procedure. For example, an adverse event such as a patient's blood pressure unexpectedly dropping may occur during a surgical procedure. Accordingly, the correlation database 116 may implement a search of all databases for data relating to unexpected drop in blood pressure during a similar surgical procedure. In accordance with this non-limiting example, the data stored in the correlation database 116 may include data indicating the percentage of patients who incur an increase in blood pressure during such a surgical procedure, as well as data correlating such occurrence of increased blood pressure to the respective patient's medical history. For example, the past history may indicate that more than 75% patients experiencing increased blood pressure were diabetic patients and that a particular injection (e.g. Hydralazine used to relax and dilate blood vessels, resulting in lowered blood pressure) proved to be effective for 90% of such patients. The correlation database 116 may also include a surgeon's annotations organized by frequency of usage of the database. For example, 70% of the surgeons may have annotated to provide said injection before proceeding to a next step.

Figure 1B:
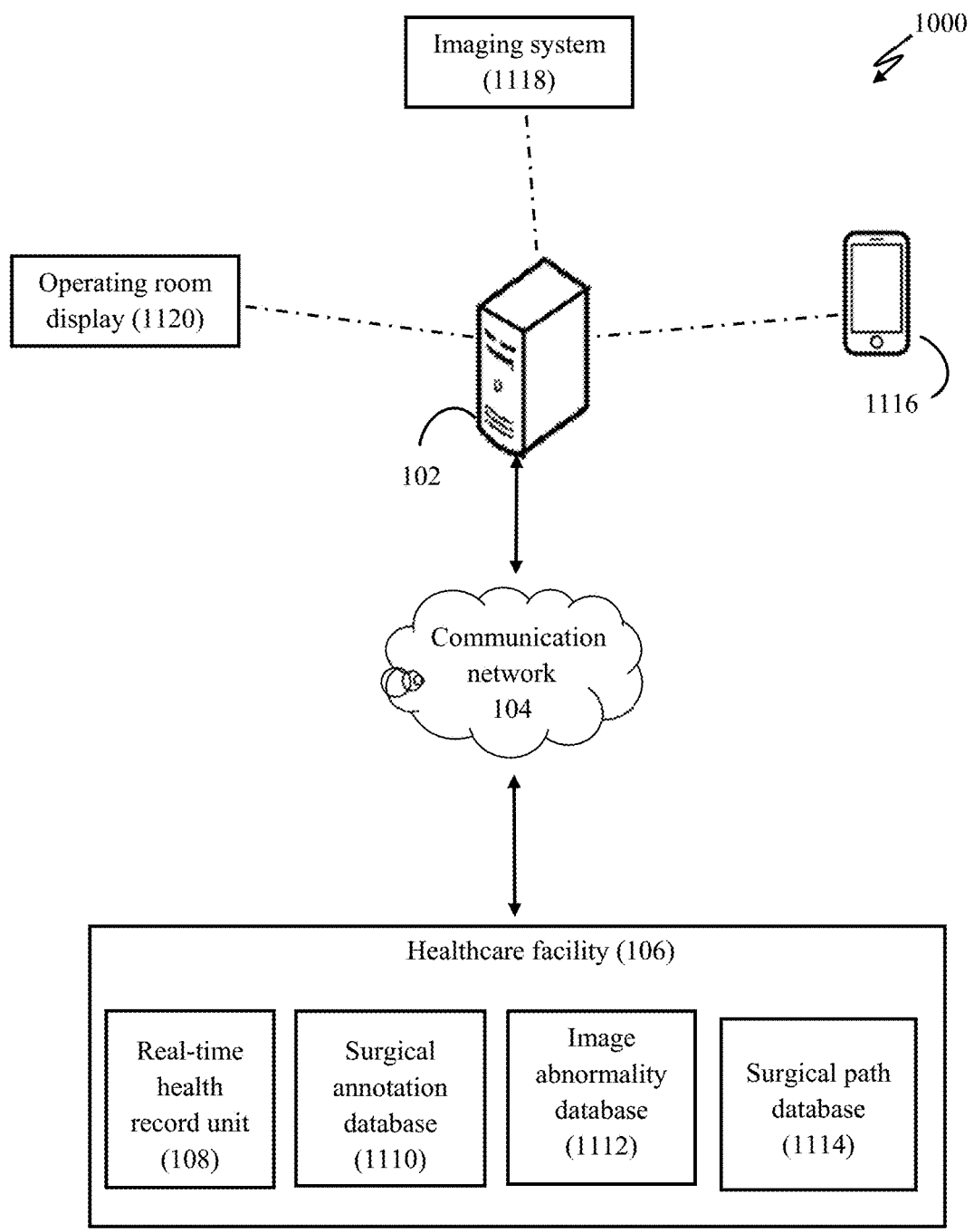
FIG. 1B illustrates a network connection diagram 1000 of a system 102 for creating a surgical plan for use in a surgical procedure, according to another embodiment.

FIG. 1B illustrates a network connection diagram 1000 of a system 1102 for creating a surgical plan for use in a surgical procedure, according to another embodiment. The system 1102 may be connected to a communication network 104, similar to that of FIG. 1A. The communication network 104 may further be connected with the healthcare facility 106 for facilitating data transfer between the system 1102 and the healthcare facility 106.

The communication network 104 may be the same or similar to that of FIG. 1A.

The healthcare facility 106 may include a real-time health record unit 108 and a group of databases for storing different information required during the surgical procedure. The group of databases may include a surgical annotation database 1110, an image abnormality database 1112, and a surgical path database 1114. As with FIG. 1A, different databases are used in present case; however, a single database may also be used for storing the data. Usage of the different databases may also allow segregated storage of different data and may thus reduce time to access required data.

The real-time health record unit 108 may be configured to store medical data for a plurality of patients in real-time. The data may correspond to a respective patient's medical imaging data, diagnostic data, as well as comprehensive medical history data. The stored medical data may include medical images of an affected body part of a respective patient, as well as comprehensive medical records, including medical history, previous test results, and notes of surgeons/doctors or medical advisors.

In at least one embodiment, the surgical annotation database 1110 may be configured to accept annotations provided by a respective surgeon, either during surgical planning or in real-time during a surgical procedure. The surgeon may add the annotations at any time during surgical pre-operative planning, and the annotations may be stored in the surgical annotation database 1110. The surgeon may add the annotations either using the system 102 or a user device 116. A smart phone is shown as the user device 1116 in FIG. 1B, as an example, used for displaying information related to the surgical procedures. However, user device 1116 may be implemented as any other device comprising a Graphical User Interface (GUI), for example, a laptop, a desktop, a tablet, a phablet, or other such devices known in the art.

In at least one embodiment, the image abnormality database 1112 may be configured to store data related to irregularities and/or abnormalities in the medical images of the affected body part of a respective patient. The medical images may include a plurality of images captured using an imaging system 118, utilizing known medical imaging techniques, such as Magnetic Resonance Imaging (MRI), Computerized Tomography (CT), X-rays, etc. The image abnormality database 1112 may store data related to the abnormalities identified in the medical images during the pre-planning stage of a surgical procedure. A non-limiting example of such an irregularity and/or abnormality stored in image abnormality database 1112 may relate to a ruptured Achilles tendon of a right ankle of a respective patient.

In at least one embodiment, the surgical path database 1114 may be configured to store the plurality of surgical paths that may be followed for respective surgical procedures.

Figure 2A:
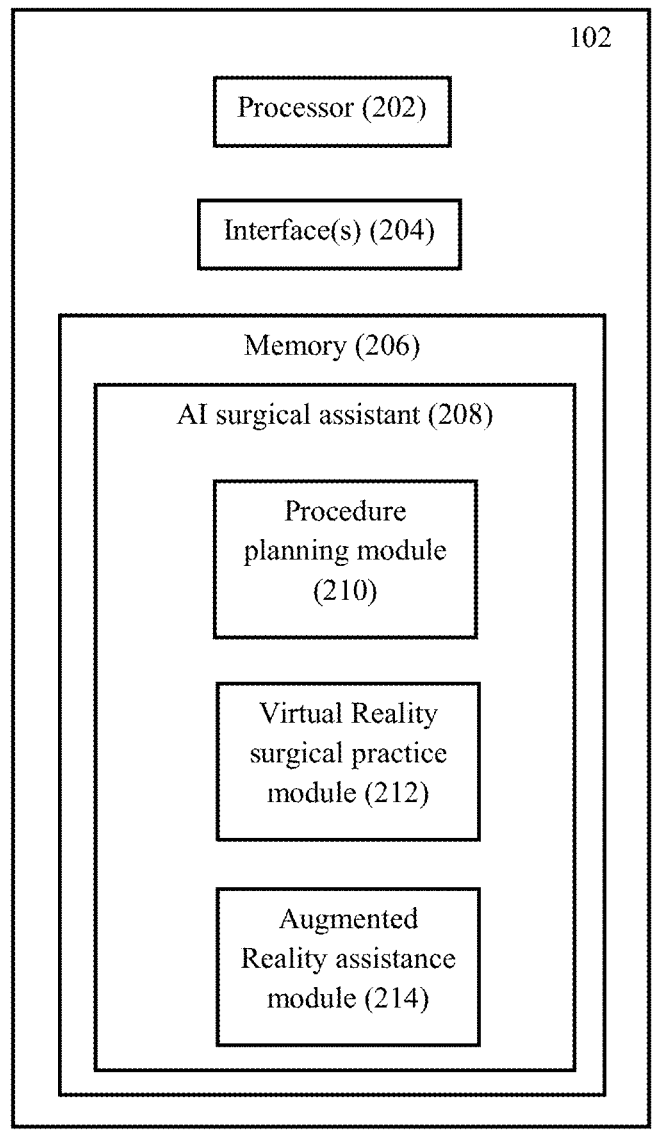
FIG. 2A shows a block diagram showing different components of the system 102, according to an embodiment.

FIG. 2A shows a block diagram showing different components of system 102 as depicted in FIG. 1A. The system 102 comprises a processor 202, interface(s) 204, and memory 206. The processor 202 may execute an algorithm stored in the memory 206 for utilizing artificial intelligence to provide surgical assistance. The processor 202 may also be configured to decode and execute any instructions received from one or more other electronic devices or server(s). The processor 202 may include one or more general purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor). The processor 202 may be configured to execute one or more computer-readable program instructions, such as program instructions to carry out any of the functions described in this description.

The interface(s) 204 may help a user to interact with the system 102. The interface(s) 204 of the system 102 may either accept an input from the user or provide an output to the user, or may perform both the actions. The interface(s) 204 may either be a Command Line Interface (CLI), Graphical User Interface (GUI), or a voice interface.

The memory 206 may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions.

The memory 206 may comprise an Artificial Intelligence (AI) surgical assistant 208, implemented as a program. The AI surgical assistant 208 may comprise three modules i.e. procedure planning module 210, virtual reality surgical practice module 212, and augmented reality assistance module 214.

Figure 2B:
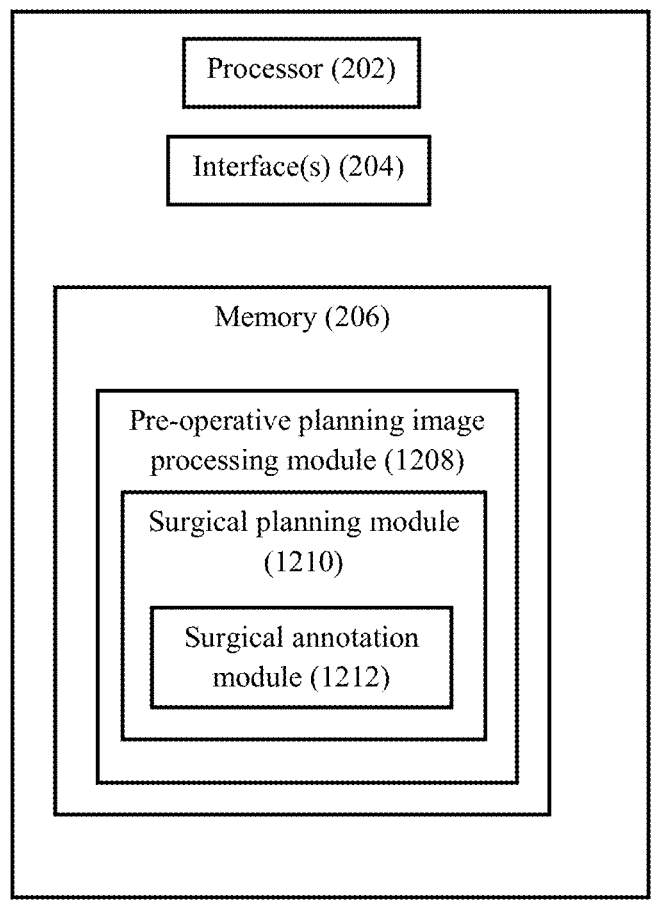
FIG. 2B shows a block diagram showing different components of the system 102, according to an embodiment.

FIG. 2B shows a block diagram showing different components of the system 1102, as depicted in FIG. 1B, according to an embodiment. The system 1102 includes a processor 202, interface(s) 204, and a memory 206, similar to that of FIG. 2A. Further to the description thereof pertaining to FIG. 2A, the processor 202 may execute an algorithm stored in the memory 206 for creating the surgical plan for use in the surgical procedure. The processor 202 may also be configured to decode and execute any instructions received from one or more other electronic devices or server(s). Again, the processor 202 may include one or more general purpose processors (e.g., INTEL® or Advanced Micro Devices® (AMD) microprocessors) and/or one or more special purpose processors (e.g., digital signal processors or Xilinx® System On Chip (SOC) Field Programmable Gate Array (FPGA) processor). The processor 202 may be configured to execute one or more computer-readable program instructions, such as program instructions to carry out any of the functions described in this description.

Further to the description thereof pertaining to FIG. 2A, the interface(s) 204 may facilitate a surgeon's interaction with the system 102. The interface(s) 204 of the system 102 may accept input from the surgeon and provide an output to the surgeon. The interface(s) 204 may either be a Command Line Interface (CLI), Graphical User Interface (GUI), or a voice interface.

Again, similar to the description thereof pertaining to FIG. 2A, the memory 206 may include, but is not limited to, fixed (hard) drives, magnetic tape, floppy diskettes, optical disks, Compact Disc Read-Only Memories (CD-ROMs), and magneto-optical disks, semiconductor memories, such as ROMs, Random Access Memories (RAMs), Programmable Read-Only Memories (PROMs), Erasable PROMs (EPROMs), Electrically Erasable PROMs (EEPROMs), flash memory, magnetic or optical cards, or other type of media/machine-readable medium suitable for storing electronic instructions.

In one embodiment, the memory 206 may include a pre-operative planning image processing module 1208. The pre-operative planning image processing module 1208 includes a surgical planning module 1210. Further, the surgical planning module 1210 includes a surgical annotation module 212.

Figure 3A:
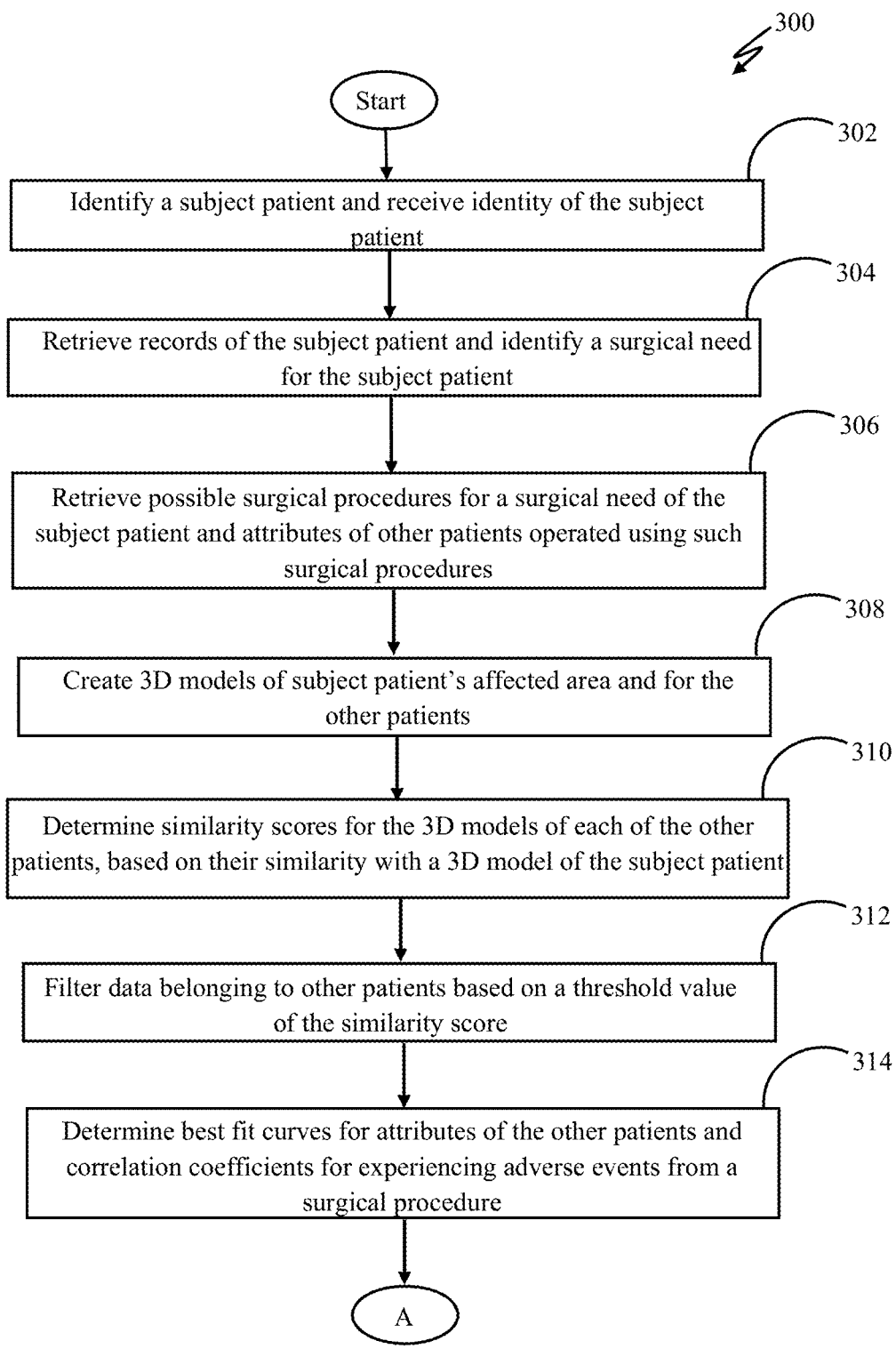
FIGS. 3A and 3B collectively illustrate a flowchart 300 showing a method executed by procedure planning module 210 of the system 102, according to an embodiment.
Figure 3B:
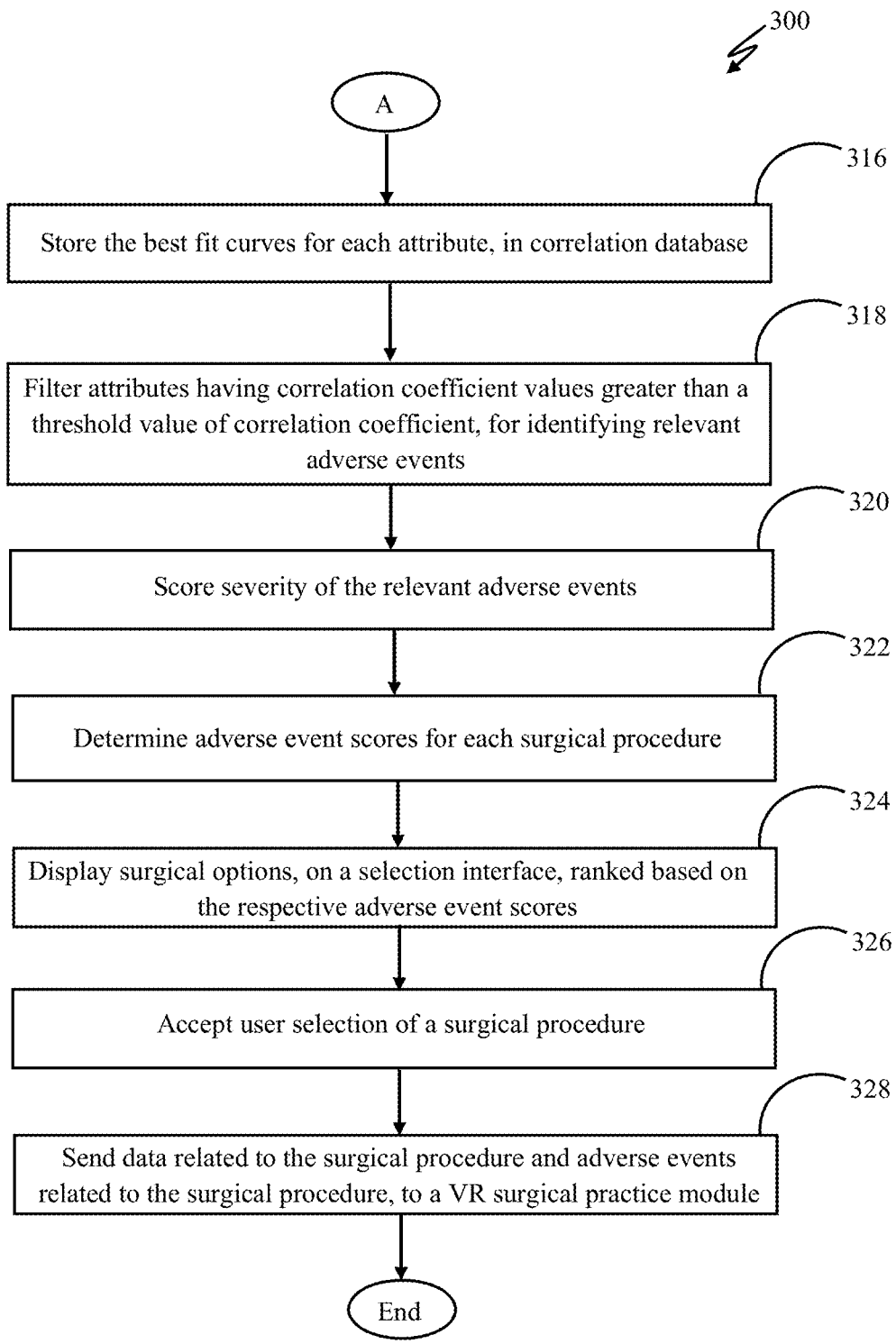

Functioning of the procedure planning module 210, as shown in FIG. 2A, will now be explained with reference to flowchart 300 shown in FIGS. 3A and 3B. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

A user may log into the procedure planning module 210. The term "user" may refer to a surgeon, and may henceforth be used interchangeably in the description. Optionally, the logging in procedure may be accompanied with authentication of the user. Upon logging in, the procedure planning module 210 may allow the user to identify a subject patient and receive identification information for the subject patient, at step 302. The subject patient may refer to a patient upon whom the surgeon will operate. The procedure planning module 210 may be utilized to retrieve records pertaining to the subject patient from Electronic Health Records (EHR) stored in real-time health record unit 108.

Thus, step 304 includes retrieving records of the subject patient, and identifying the surgery to be performed for the subject patient. As an example of a surgery that may be performed, the subject patient may need an Anterior Cruciate Ligament (ACL) repair of his left knee. All possible surgical procedures for repairing of the knee may thus be retrieved from the surgical options database 112. Further to the example, the surgical procedure for repairing the knee may include a cadaver graft, patellar tendon graft, and different methods of performing such surgical procedures. The surgical procedures may be performed though arthroscopy, open, and/or other different surgical paths of going in on one side of the knee and another side of the knee. Also retrieved from surgical options database 112 at step 306, along with the possible surgical procedures, are attributes of other patients operated upon using such surgical procedures as well as details of adverse events that have occurred or may occur during such surgical procedures.

At step 308, the procedure planning module 210 may create Three-dimensional (3D) models of both the subject patient's affected area as well as that for the other patients whose comparative data was retrieved. At step 310, the 3D model of the subject patient may be compared to the 3D models of the other patients to determine similarity scores. At step 312, data belonging to the other patients may be filtered based on a threshold value of the determined similarity scores. As a non-limiting example, the threshold similarity score value may be set as 25%, thus, data belonging to the other patients, present in the top 25% of the similarity scores may be kept for further analysis.

Step 314 includes determining best fit curves for attributes of the remaining ones of the comparative patients. For example, Body Mass Index (BMI) may be used as an attribute of the the remaining ones of the comparative patients. Step 314 may also include determining correlation coefficients for experiencing adverse events from a surgical procedure. For example, blood loss during surgery may be one such adverse event. Thereafter, step 316 includes storing best fit curves for each attribute in the correlation database 116.

Step 318 includes filtering the attributes based on a threshold value of correlation coefficient. As a non-limiting example, the attributes having correlation coefficient values greater than the threshold value of correlation coefficient may be filtered for further use. Thus, if the threshold value of correlation coefficient is set at 0.6, the attributes having correlation coefficient values less than 0.6 may be discarded. Step 318 also includes identifying relevant adverse events based on the filtering. The attributes in which the subject patient's attribute measurement lies outside of a standard deviation from a best fit curve may also be discarded.

Step 320 includes scoring a severity of the relevant adverse event may be scored. As a non-limiting example, the score may range from 1 to 10, by which 1 may indicate a lowest level of severity and 10 may indicate a highest level of severity. The severity scores for adverse events may be determined based on predefined rules, as severity of any adverse event is well known to the surgeons.

At step 322, adverse event scores may be determined for each surgical procedure previously identified at step 306 by multiplying a correlation coefficient of an attribute, present in common with the subject patient, by a severity score of the adverse event. For example, the correlation coefficient between BMI greater than 35 and bleeding during patellar tendon graft may be 0.8, and the severity score may have a value of 3. The severity of the adverse event during such case may be scored as "0.8*3=2.4." In accordance with a non-limiting example, the score of 2.4 may be summed with scores of all other adverse events. It is evident that all such scores are pre-determined for adverse events, and thus the adverse events occurring in a real surgical procedure may have corollary scores.

Figure 4:
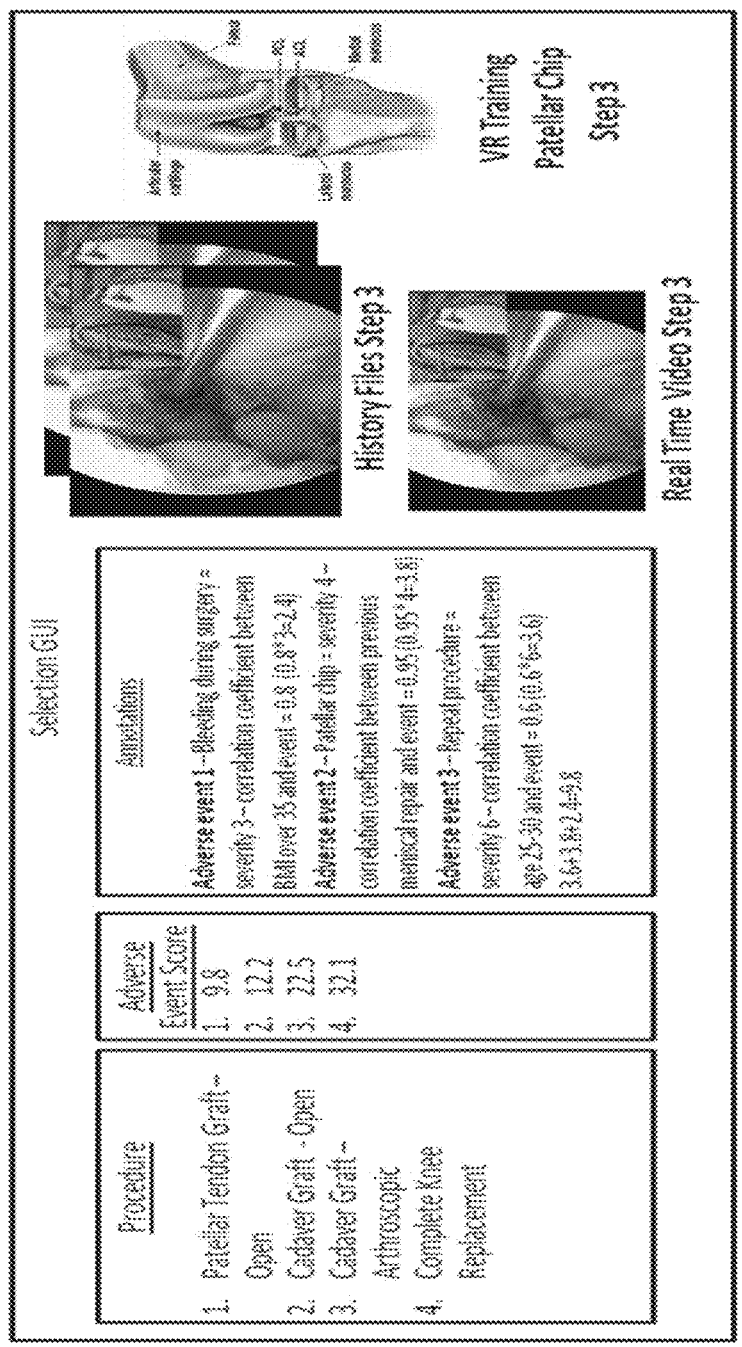
FIG. 4 illustrates a Graphical User Interface (GUI) of a user device 120, presenting information related to surgical procedures, according to an embodiment.

FIG. 4 shows a non-limiting example of information related to the surgical procedures being displayed on a Graphical User Interface (GUI) of a user device 120 such as the smart phone shown as the user device 120 in FIG. 1. However, the user device 120 used to display information related to the surgical procedures may be any other device comprising a GUI, for example, a laptop, a desktop, a tablet, a phablet, or other such devices known in the art.

Step 324 of flowchart 300 continues, with reference to FIG. 4, by ranking the surgical procedures based on the respective adverse event scores. The surgical procedures may be displayed on the GUI with the adverse events being listed from top to bottom in ascending order of adverse event scores. A user may then select one surgical procedure from amongst the available surgical procedures, and step 326 includes a user selection of the surgical procedure being accepted through the GUI.

In one embodiment, using the GUI, the user may view plurality of information in real-time, during the surgical procedure. The plurality of information may include the possible surgical procedures, currently adopted surgical procedure, adverse events ranked on the basis of their scores, annotations related to the adverse events, associated files history for an adverse event (for example, Patellar chip in present case), procedure to be followed at a current step to move ahead, and a real-time video of each step performed. Further, all images displayed on the GUI may be overlaid, scaled, and annotated by the user. Thus, step 328 includes sending to Virtual Reality (VR) surgical practice module 212 the data related to the surgical procedure and adverse events related to the surgical procedure.

The VR surgical practice module 212 may allow a user to work on VR surgical practice equipment 122, which may be connected to the system 102, and may allow simulation of surgical procedures. The simulation may include displaying one or more virtual organs to be operated upon by the user. A vital organ may comprise multiple elements and each element may have neighbouring elements. A plurality of tensioned connections may connect the neighbouring elements with the vital organ, such that force applied on one element propagates via respective neighbouring elements and thus providing a distributed reaction over the vital organ.

The VR surgical practice equipment 122 may also include a physical manipulation device for manipulation by the user and a tracking arrangement for tracking the physical manipulation device and translating motion of the physical manipulation device into application of forces onto said virtual organ. The VR surgical practice equipment 122 facilitates simulation of moving, cutting, suturing, coagulations, and other aspects of surgical procedures for different organs. Thus, the VR surgical practice equipment 122 may facilitate surgical practice for a user.

Figure 5:
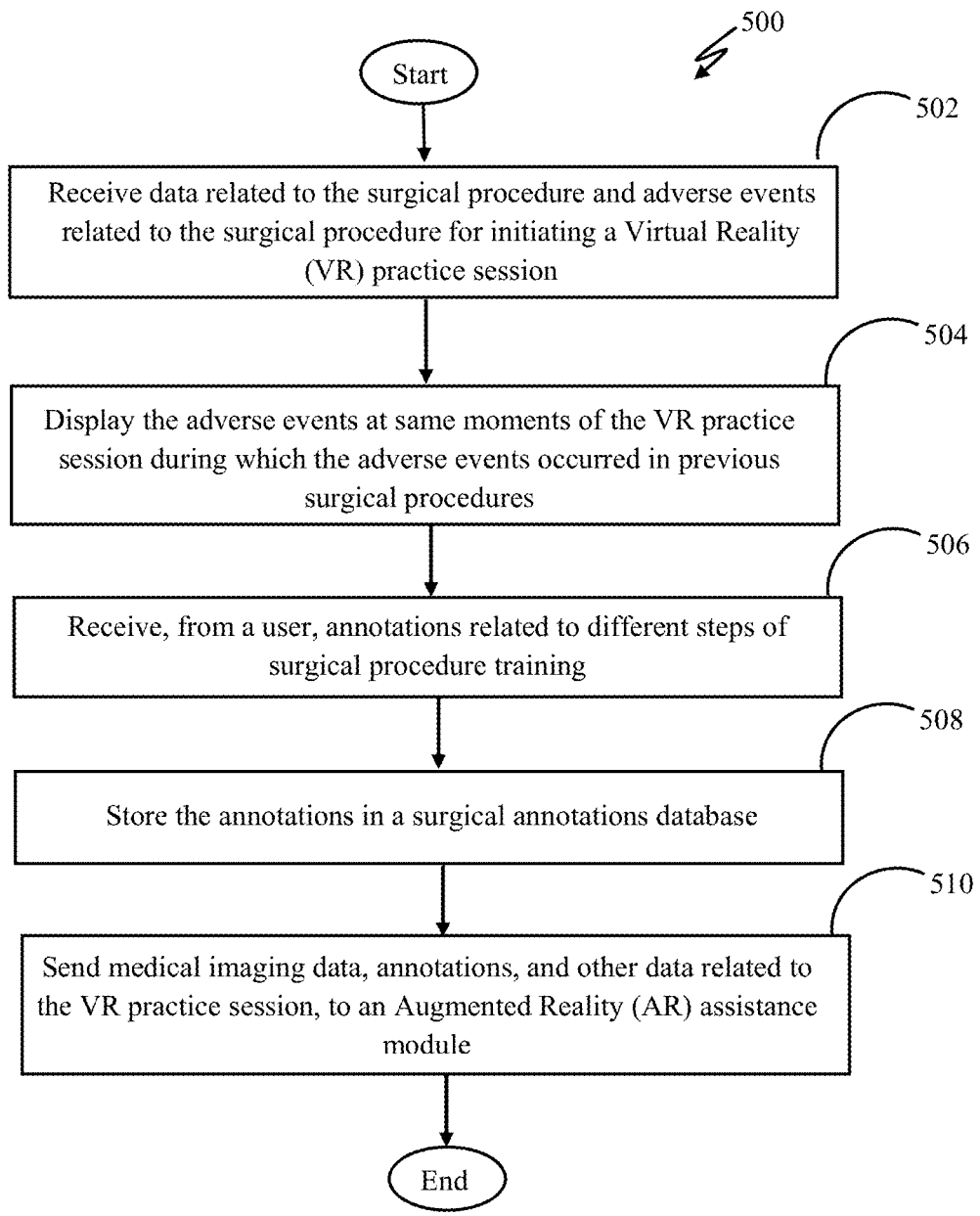
FIG. 5 illustrates a flowchart 500 showing a method executed by Virtual Reality (VR) surgical practice module 212 of the system 102, according to an embodiment.

FIG. 5 illustrates a flowchart 500 for a method executed by VR surgical practice module 212, as shown in FIG. 2A. A user may log into the system 102 using VR surgical practice equipment 122. At step 502, the VR surgical practice module 212 may receive data related to the surgical procedure and adverse events related to the surgical procedure. The user may start VR practice session using the augmented reality display 118 and the VR surgical practice equipment 122, based on the data received from the procedure planning module 210.

Step 504, during the VR practice session, includes the data pertaining to possible adverse events being displayed to the user in synchronism with the same moments during the practice session at which the adverse events actually occurred in previous surgical procedures. At step 506, the user may provide annotations related to different steps of surgical procedure training. The annotations may be made in various formats including, but not limited to, text, audio notes, instructions to pull up specific medical data from patient's Electronic Health Records (EHR), and Audio-Video files related to the procedure. At step 508, the annotations may be stored in the surgical annotations database 114. At step 510, the medical imaging data, annotations, and other data related to the VR practice session may be sent to the Augmented Reality (AR) assistance module 214.

Figure 6:
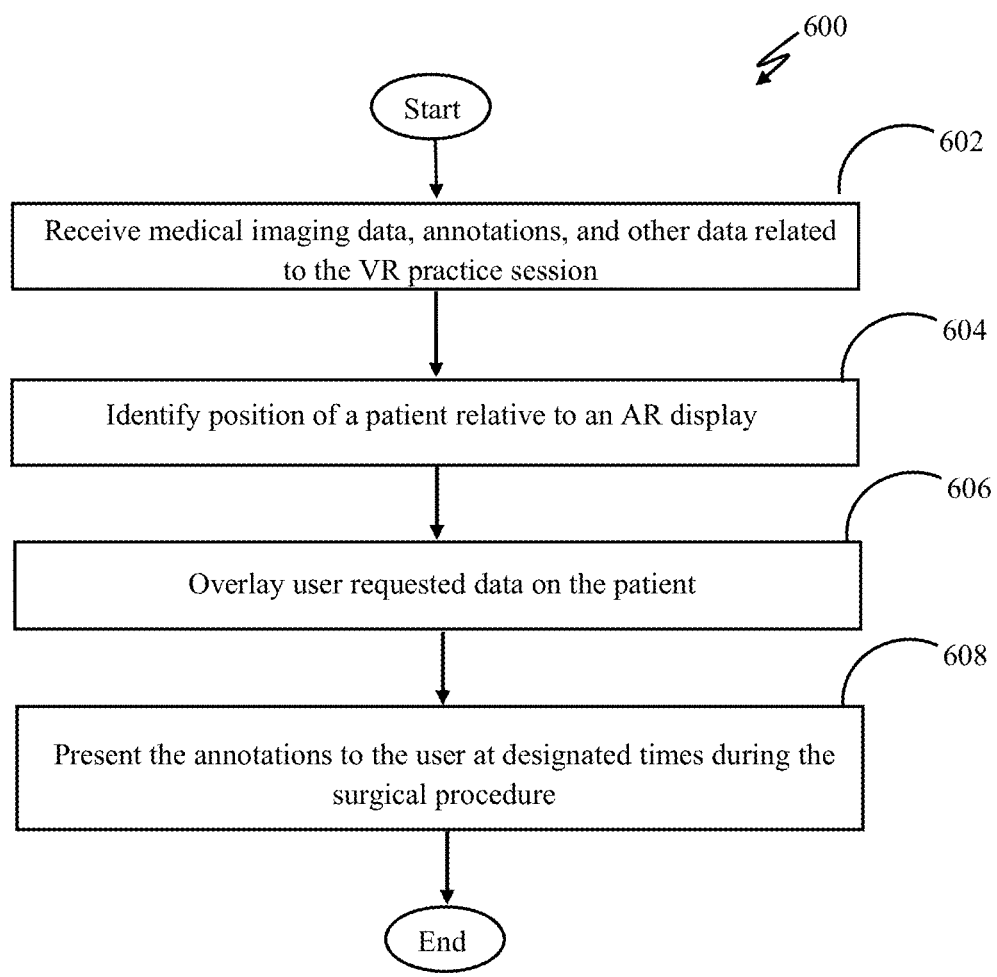
FIG. 6 illustrates a flowchart 600 showing a method executed by Augmented Reality (AR) assistance module 214 of the system 102, according to an embodiment.

FIG. 6 shows a flowchart 600 for a method executed by AR assistance module 214 in FIG. 2A. The AR assistance module 214 may support the user while performing the real surgical procedure on the subject patient. At step 602, the AR assistance module 214 may receive the medical imaging data, annotations, and other data related to the VR practice session. At step 604, a position of the patient may be identified relative to an AR display 118 worn by the user. Based on the identified position, at step 606, user requested data may be overlaid on the portion.

In at least one non-limiting example, at step 608, the user may start performing the surgical procedure on the patient, and the annotations may be presented to the user at designated times. By at least one example embodiment, time stamps may be used to determine an appropriate time to present the annotations. For example, an annotation may be set to be presented five minutes into the surgical procedure.

Alternatively, an appropriate time to present the annotations may be determined based upon initiation of a particular step of a surgical procedure. For example, an annotation may be set to be presented during initiation of a third step of the surgical procedure. Each step of the surgical procedure may be monitored by the AR display 118, and thus the system 102 may present the annotation to the user during a predetermined step.

The annotations may help the surgeon by storing important details related to any step of the surgical procedure, which may then be recalled during subsequent procedures. Such details may be presented to the surgeon, at designated moments, for reminding about taking due care, as annotated. Thus, the surgeons may be assisted by their own person input defined during a training session prior to the actual surgical procedure. This helps in improving accuracy of the surgeons by allowing them to utilize every minute yet essential detail, thus reducing occurrence of adverse events experienced by the patient, during a surgical procedure.

Figure 7:
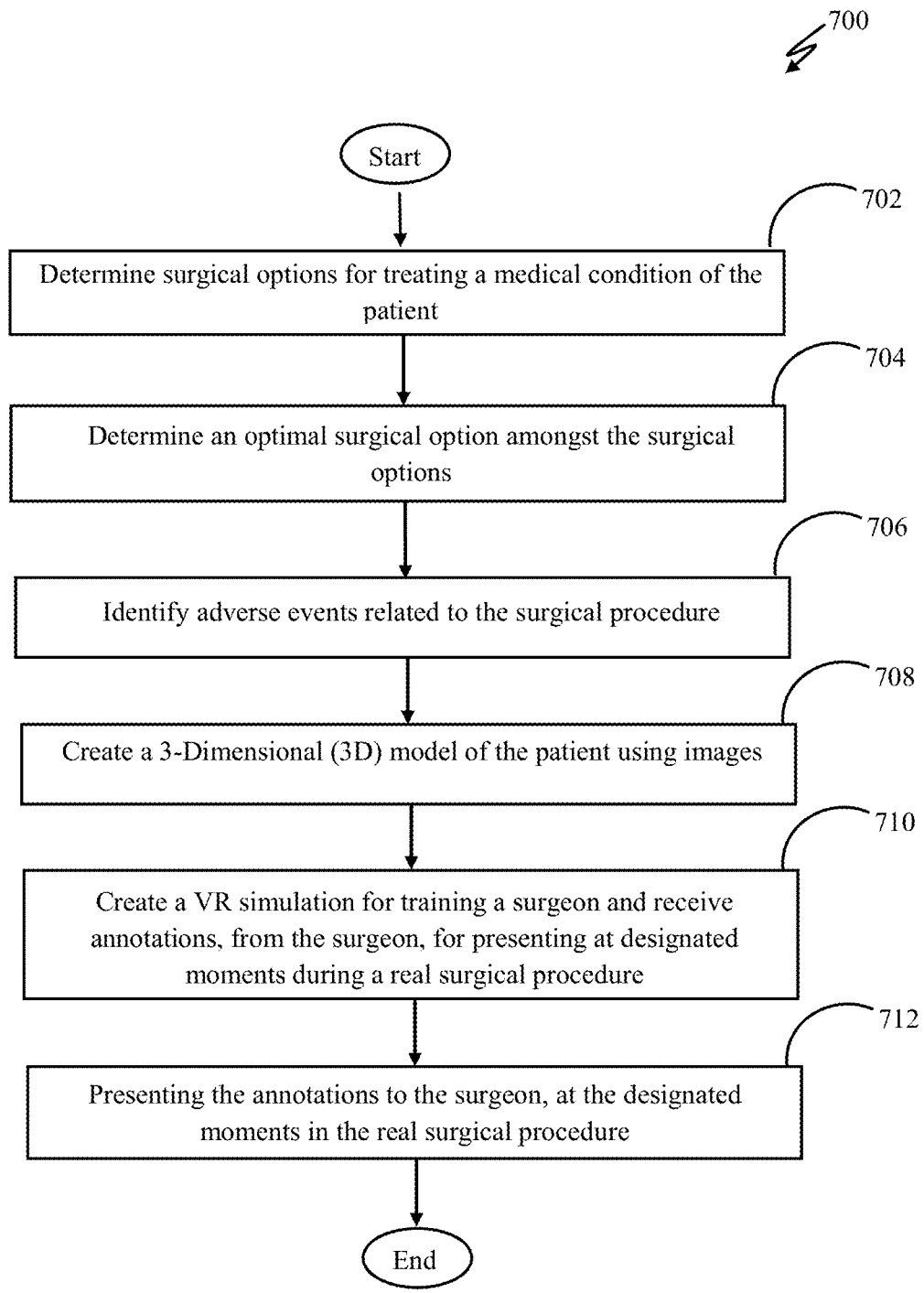
FIG. 7 illustrates a method 700 of providing surgical assistance during a surgical procedure, according to an embodiment.

FIG. 7 shows a flowchart 700 for a method of providing surgical assistance during a surgical procedure, according to an embodiment of system 102 as shown in FIG. 2A.

In flowchart 700, each block may represent a module, segment, or portion of code, which comprises one or more executable instructions for implementing a respective specified logical function(s). In some alternative implementations, the functions noted in the blocks may occur in a different order than that shown in FIG. 7. For example, two blocks shown in succession may in fact be executed substantially concurrently or the blocks may be executed in reverse order, depending upon the functionality involved. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure such as a state machine. The flowchart 700 starts at the step 702 and proceeds to step 712.

At step 702, a medical condition of a patient may be determined. Based on the medical condition, surgical options may be determined for the patient. In one embodiment, the surgical options may be determined by processor 202 of the system 102, as shown in FIG. 2A, in communication with the surgical options database 112.

At step 704, an optimal surgical option may be determined from among the stored surgical options based on outcomes of the surgical options in other patients. In one non-limiting example, the optimal surgical option may be determined by the processor 202.

At step 706, adverse events related to the surgical procedure may be identified. In one non-limiting example, the adverse events may be identified by the processor 202.

At step 708, a Three-Dimensional (3D) model of the patient may be created using images of the patient gathered from one or more of different sources such as a digital camera, X-ray device, and Magnetic Resonance Imaging (MRI) device. In one non-limiting example, the 3D model may be created by the processor 202.

At step 710, a Virtual Reality (VR) simulation may be created for training a surgeon using the 3D model. During the training, annotations may be received from the surgeon and stored in the surgical annotations database 114. The annotations may later be presented to the surgeon at designated moments during a real surgical procedure. The designated moments may be set based on time-stamps or steps of an actual surgical procedure. In one non-limiting example, the VR simulation may be created and the annotations may be accepted by the processor 202.

At step 712, the annotations may be presented to the surgeon at the designated moments of an actual surgical procedure. The annotations provide surgical assistance to the surgeon by providing reminders of certain important activities and details to be implemented at the designated moments. In one non-limiting example, the annotations may be visually presented by a user interface.

Figure 8:
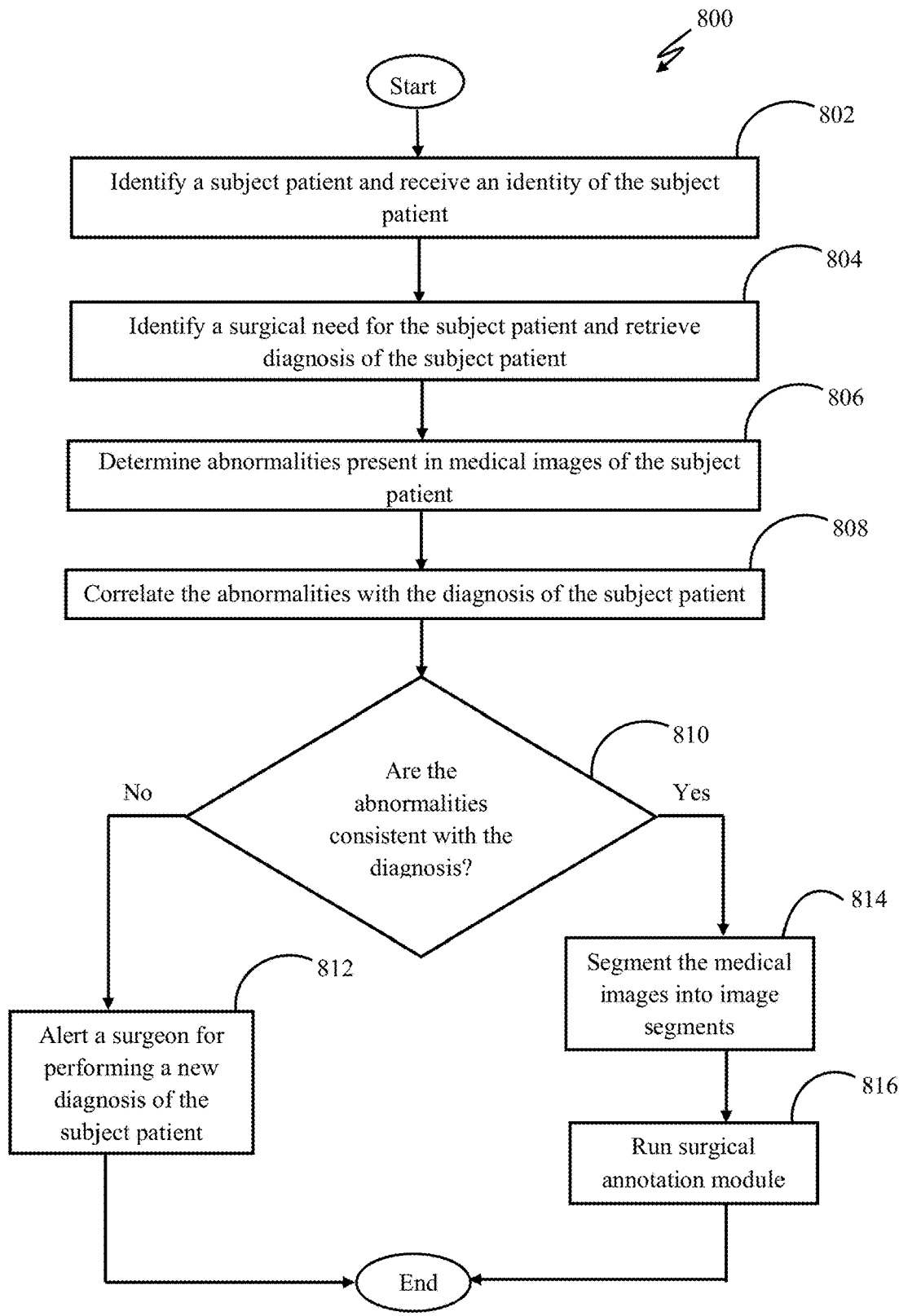
FIG. 8 illustrates a flowchart 300 showing a method performed by a surgical planning module 210 of the system 102, according to an embodiment.

Functioning of the surgical planning module 1210, as shown in FIG. 2B, will now be explained with reference to flowchart 800 shown in FIG. 8, with reference to system 1102 of FIGS. 1B and 2B. The functions performed in the processes and methods may be implemented in differing order than those presently depicted and described. Furthermore, the outlined steps and operations are only provided as examples, and some of the steps and operations may be optional, combined into fewer steps and operations, or expanded into additional steps and operations without detracting from the essence of the disclosed embodiments.

At first, the surgeon may need to log-in to the surgical planning module 1210. The surgeon may log-in using his credentials, i.e., a user name and a password, using, for example, the user device 1116. Upon log-in, the surgical planning module 1210 may facilitate the surgeon identifying a subject patient and receiving identification information for the subject patient, at step 802. The surgical planning module 1210 may be utilized to retrieve medical data pertaining to the subject patient from Electronic Health Records (EHR) stored in the real-time health record unit 1108. The medical data may include medical images of an affected body part of the subject patient, as captured by the imaging system 1118 using one or more medical imaging techniques, such as Magnetic Resonance Imaging (MRI), Computerized Tomography (CT), and X-Ray.

At step 804, a recommendation for surgery for the subject patient may be made, and the diagnosis of the subject patient may be retrieved based at least on the subject patient's medical data. At step 806, any abnormalities present in the medical images may be identified; and at step 808, the identified abnormalities may be correlated with the diagnosis of the subject patient.

At decision block 810, the surgical planning module 1210, shown in FIG. 2B, may be utilized to determine whether the identified abnormalities and the subject patient's diagnosis are consistent with each other. At step 812 ("no"), if the identified abnormalities are not consistent with the subject patient's diagnosis, the surgical planning module 1210 may be utilized to alert the surgeon that a diagnosis is needed for the subject patient. At step 814 ("yes"), In case the identified abnormalities are determined to be consistent with the subject patient's diagnosis, the surgical planning module 1210 may be utilized to segment the medical images. Thereafter, at step 816, the surgical planning module 1210 may be utilized to run the surgical annotation module 1212.

Figure 9:
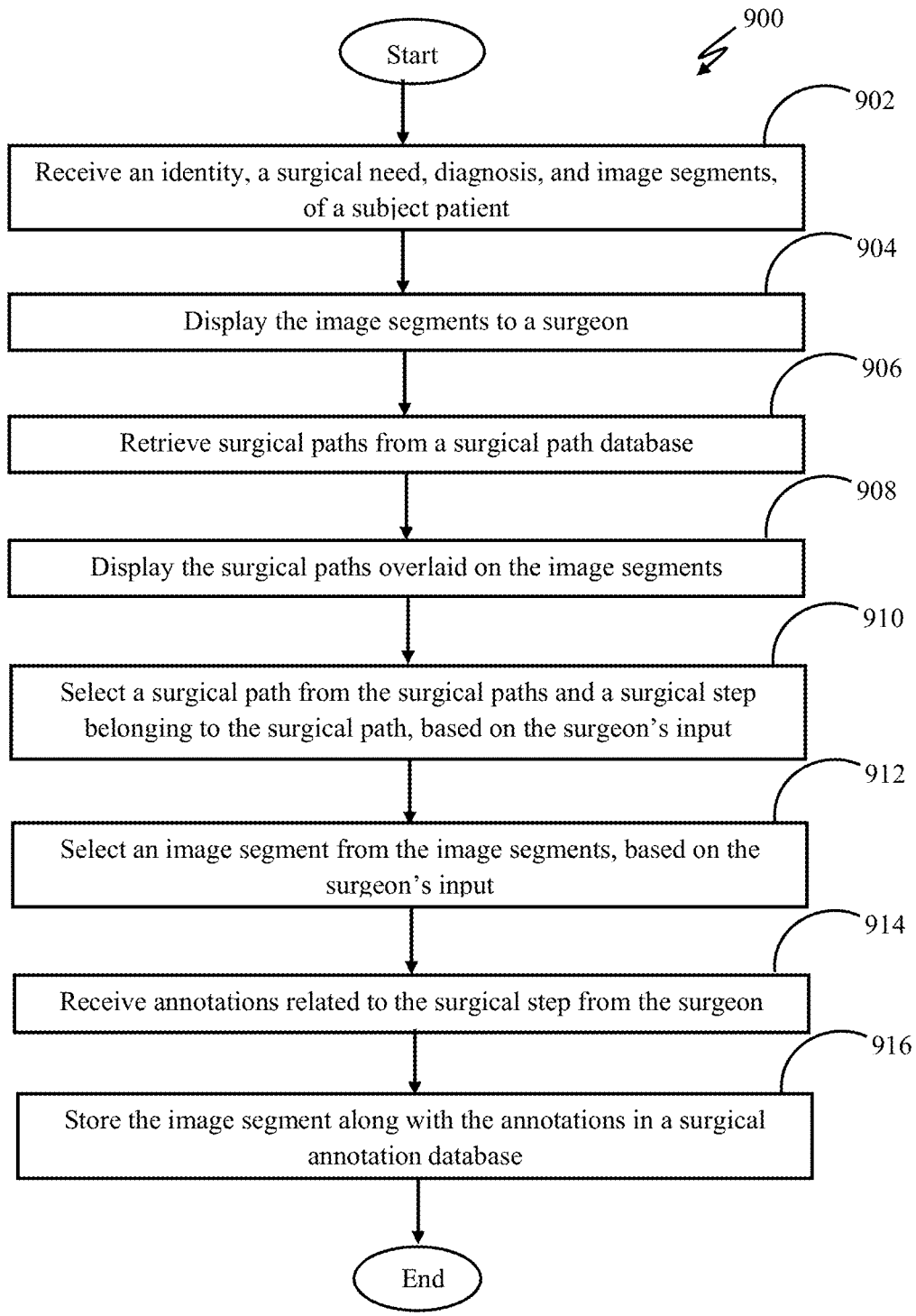
FIG. 9 illustrates a flowchart 400 showing a method performed by a surgical annotation module 212 of the system 102, according to an embodiment.

Functioning of the surgical annotation module 1212, as shown in FIG. 2B, will now be explained with reference to the flowchart 900 shown in FIG. 9, with reference to system 1102 of FIGS. 1B and 2B. Once again, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 10A:
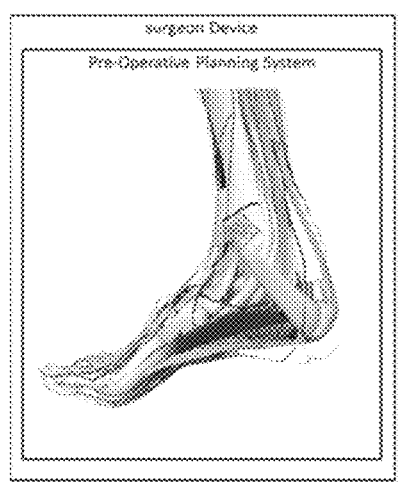
FIGS. 10A-10F collectively illustrate a Graphical User Interface (GUI) 500 of a user device 116 connected to the system 102, presenting information related to the surgical procedure, according to an embodiment.

At step 902, the surgical annotation module 1212 may receive identification information for the subject patient, the recommended surgery for the subject patient, the subject patient's diagnosis, and the image segments, from the surgical planning module 1210, shown in FIG. 2B. At step 904, the surgical annotation module 1212 may be utilized to display the image segments for the surgeon. The image segments may be displayed on the GUI of the user device 1116. For example, as shown in FIG. 10A, segment of an affected body part, i.e., a ruptured Achilles tendon of a right ankle of the subject patient, is displayed to the surgeon.

At step 906, the surgical paths may be retrieved from the surgical path database 1114 based on criteria set by the surgeon, including, but not limited to, frequency of success of the surgical paths, time of operation for the surgical paths, etc. Thereafter, the surgical paths may be overlaid on the image segments of the affected body part of the subject patient.

Figure 10B:
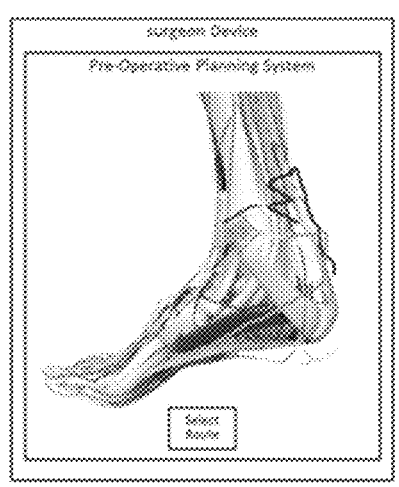

At step 908, the surgical paths that are overlaid on the image segments may be displayed for the surgeon using the GUI of the user device 1116. For example, as shown in FIG. 10B, the surgical paths overlaid on an image segment of the affected body part, i.e., the ruptured Achilles tendon of the right ankle of the subject patient, is displayed in different colors, such as red, green, yellow, etc.

Figure 10C:
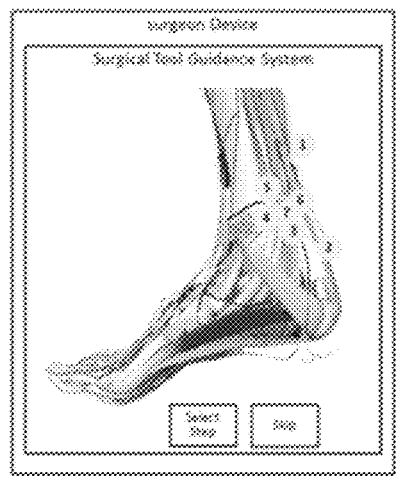

At step 910, a surgical path may be selected from the surgical paths, and a surgical step belonging to the surgical path may be selected based on the surgeon's input. For example, as shown in FIG. 10B, the surgical paths may be displayed to the surgeon for selecting a surgical path, i.e., a route. Further, as shown in FIG. 10C, the surgical steps may be displayed to the surgeon to select a surgical step in order to repair the right knee of the subject patient.

Figure 10D:
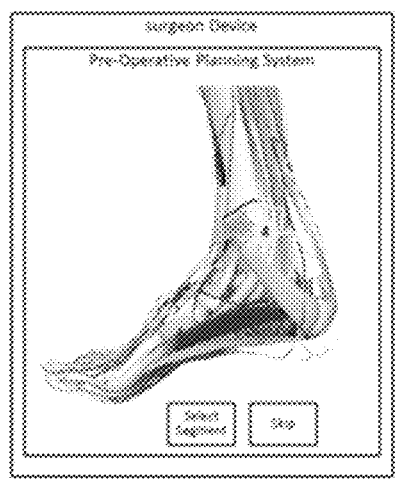

In one non-limiting example, the surgeon may select the surgical step based at least on criteria, including but not limited to average time of the surgical step and worst-case risks of the surgical step. In one non-limiting example, as shown in FIG. 10D, the surgical annotation module 1212 may be utilized to display the selected surgical step, i.e., surgical step 4 for the surgeon on the GUI of the user device 1116.

Figure 10E:
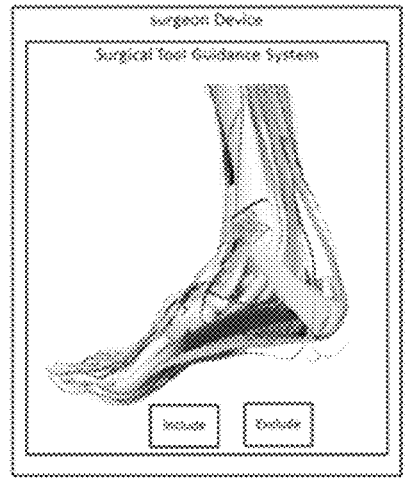

At step 912, an image segment may be selected from the image segments, based on the surgeon's input. For example, as shown in FIG. 10D, the surgical annotation module 1212 may be utilized to enable the surgeon to select an image segment using the user device 1116. In a non-limiting example, the surgical annotation module 1212 may be utilized to enable the surgeon to include or exclude the image segments. For example, as shown in FIG. 10E, the surgical annotation module 1212 may be utilized to enable the surgeon to include or exclude the image segments related to the right ankle.

Figure 10F:
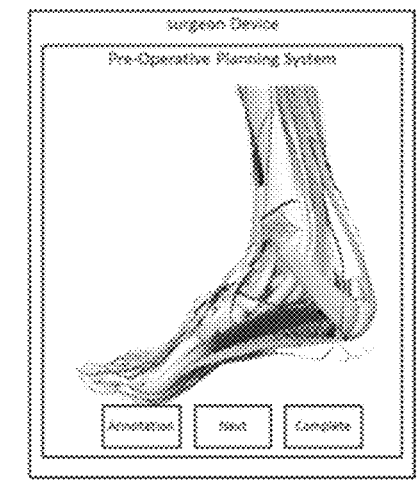

At step 914, annotations related to the surgical step may be received from the surgeon via, e.g., the GUI of the user device 1116, which may provide input options for the user. For example, as shown in FIG. 10F, the surgeon may provide an annotation, such as "to move a tibial nerve medially at the surgical step 4 to avoid contact with the tibial nerve" in order to prevent damage to the tibial nerve during execution of surgical step 4.

In another example, the surgeon may want to add an annotation at a particular surgical step regarding a particular concern pertaining to a vascular tissue in the right knee. In that example scenario, the surgeon may want to include the vascular tissue and nerve tissue but exclude specific tendons that may obscure a view of the vascular tissue and the nerve tissue. Other examples of the annotations may include requesting a 30% reduction in volume at a particular surgical step, requesting a surgical implant being added at the particular surgical step, etc.

At step 916, the image segment along with the annotations may be stored in the surgical annotation database 1110.

Figure 11:
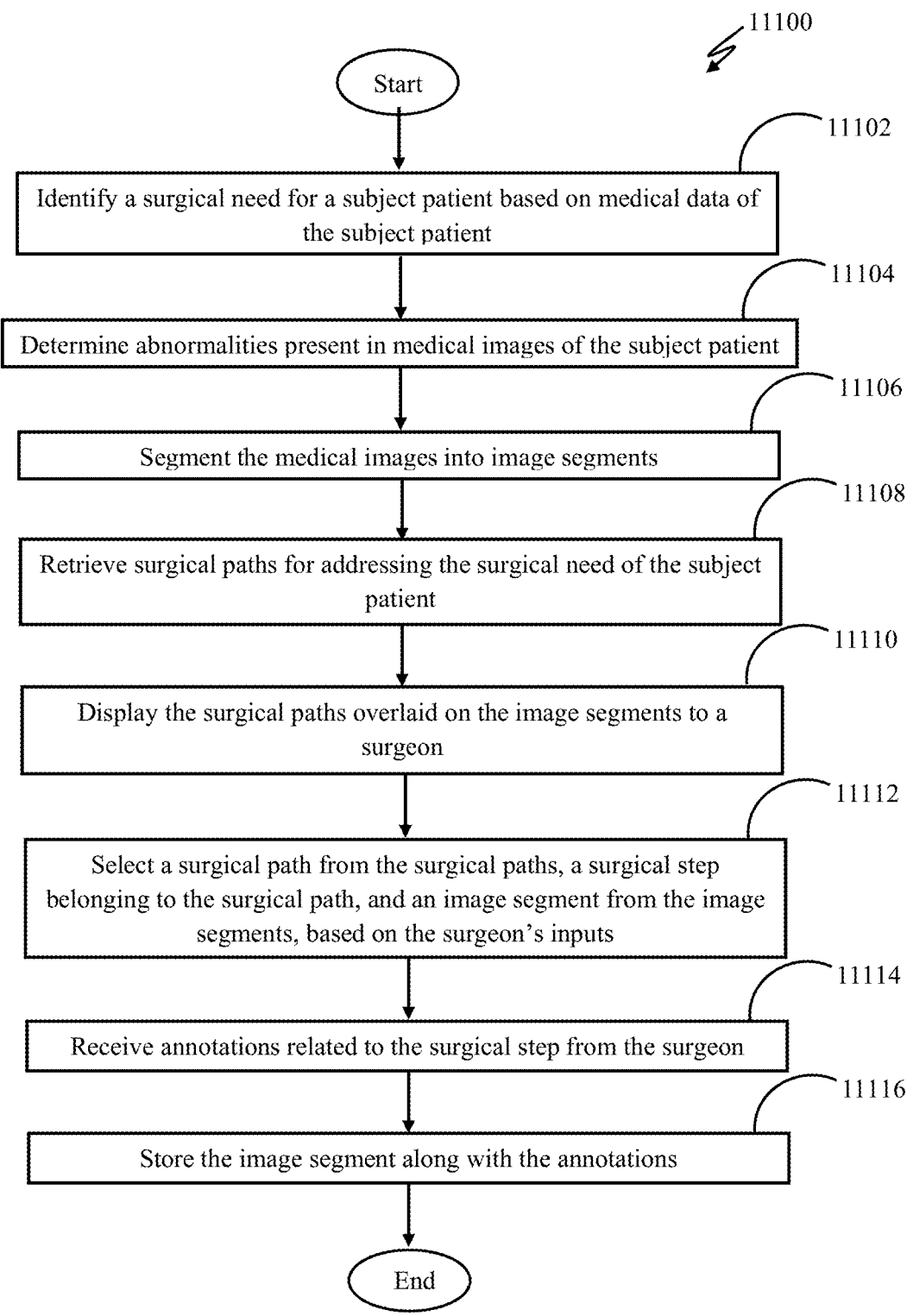
FIG. 11 illustrates a flowchart 600 showing a method for creating the surgical plan for use in the surgical procedure, according to an embodiment.

FIG. 11 a flowchart 11100 showing a method for creating the surgical plan for use in the surgical procedure, according to an embodiment, explained in conjunction with the elements disclosed in FIGS. 1B, 2B, and 10A-10F.

In flowchart 11100, each block may represent a module, segment, or portion of code, which includes one or more executable instructions for implementing a respective specified logical function(s). In some alternative implementations, the functions noted in the blocks may occur in a different order than that shown in FIG. 11. For example, two blocks shown in succession may in fact be executed substantially concurrently or the blocks may be executed in the reverse order, depending upon the functionality involved. Any process descriptions or blocks in flowcharts should be understood as representing modules, segments, or portions of code which include one or more executable instructions for implementing specific logical functions or steps in the process, and alternate implementations are included within the scope of the example embodiments in which functions may be executed out of order from that shown or discussed, including substantially concurrently or in reverse order, depending on the functionality involved. In addition, the process descriptions or blocks in flow charts should be understood as representing decisions made by a hardware structure, such as a state machine. The flowchart 11100 starts at step 11102 and ends at step 11116.

At step 11102, a recommended surgery for a subject patient may be identified based at least on medical data of the subject patient, which may include one or more medical images of an affected body part of the subject patient.

At step 11104, one or more abnormalities present in the one or more medical images of the subject patient may be identified.

At step 11106, the one or more medical images may be segmented into one or more image segments.

At step 11108, surgical paths may be retrieved for addressing the surgical need of the subject patient from the surgical path database 1114, shown in FIG. 1B.

At step 11110, the surgical paths overlaid on the one or more image segments may be displayed for the surgeon on the user device 1116.

At step 11112, a surgical path may be selected from the surgical paths, a surgical step belonging to the surgical path may be selected, and an image segment from may be selected the one or more image segments, based on the surgeon's input.

At step 11114, one or more annotations related to the surgical step may be received from the surgeon.

At step 11116, the image segment may be stored along with the one or more annotations, in the surgical annotation database 1110, thereby creating the surgical plan for use in the surgical procedure. Thereafter, the surgical plan may be displayed on an operating room display 1120 during the surgical procedure.

In an illustrative embodiment, any of the operations, processes, etc., described herein may be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected, e.g., hardware, software, and/or firmware, and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method for performing an image-guided surgical procedure, the method comprising:
  identifying surgical procedures to perform on an organ of a patient having an identified condition based on at least one previous procedure that treated other patients having the identified condition, including:
    retrieving comparative data of the other patients having the identified condition with respect to the organ;
    creating a three-dimensional (3D) model of an affected area of the patient and a comparative 3D model of the affected area of the other patients;
    determining similarity scores based on a comparison between the 3D model of the affected area of the patient and the 3D model of the affected area of the other patients; and
    filtering data of the other patients based on a threshold value of the similarity scores to produce a set of comparative patients;
  determining attributes for the set of comparative patients;
  determining correlation coefficients for at least one adverse event that may occur during respective ones of the surgical procedures and occurrences of the at least one adverse event;
  determining a plurality of surgical paths to the organ to address the identified condition;
  determining adverse event scores for each of the plurality of surgical paths based on a relationship between the correlation coefficients and the attributes;
  rearranging the plurality of surgical paths based on a ranking from the determined adverse event scores;
  selecting a surgical path for treating the identified condition to perform on the organ of the patient by a surgeon based on the ranking of the determined adverse event scores;
  producing a digital simulation of the selected surgical path to the organ for the patient;
  performing the selected surgical path to the organ on the digital simulation of the patient,
    wherein the digital simulation comprises at least one of a virtual reality (VR) simulation and an augmented reality (AR) simulation,
    wherein during the digital simulation data pertaining to at least one adverse event is displayed during the simulated selected surgical path;
  receiving and providing annotations at designated moments during the digital simulation including attaching a time stamp to respective ones of the annotations that corresponds to at least a point in time during the digital simulation at which the respective annotations are received or provided, wherein the annotations include particular surgical steps to avoid the at least one adverse event:

performing an image-guided surgical procedure based on the selected surgical path on the patient to treat the organ having the identified condition; and presenting the annotations that include the particular surgical steps to avoid the at least one adverse event at designated times during the image-guided surgical procedure.

2. The method of claim 1, wherein the annotations comprise at least one of audio files, video files, and text files.

3. A non-transitory computer-readable medium for performing an image-guided surgical procedure, storing executable instructions that, when executed, cause one or more processors to:

compile data regarding study patients who have undergone surgical procedures for surgery on an organ of a subject patient having an identified condition;

produce a three-dimensional (3D) model of an affected area of the subject patient's body and 3D models of the study patients;

determine similarity scores based on a similarity of the 3D model of the affected area of the subject patient and the 3D models of the study patients;

filter data of the study patients based on a threshold value of the similarity scores to produce a set of comparative patients;

determine attributes for the set of comparative patients;

determine correlation coefficients for at least one adverse event that occurs during the surgical procedures for the set of comparative patients and occurrences of the at least one adverse event;

determine a plurality of surgical paths to the organ to address the identified condition for the surgical Procedures;

determine adverse event scores for each of the plurality of surgical paths based on a relationship between the correlation coefficients and the attributes;

present a ranking of the plurality of surgical paths for the subject patient based on the determined adverse event scores;

rearrange the plurality of surgical paths for the subject patient based on the rankings;

select a surgical path to treat the identified condition that is to be performed on the organ of the subject patient based on the ranking of the plurality of surgical paths;

produce a digital simulation of the selected surgical path to the organ for the subject patient, wherein the digital simulation comprises at least one of a virtual reality (VR) simulation and an augmented reality (AR) simulation, wherein during the digital simulation, data pertaining to at least one adverse event is displayed during the simulated selected surgical path;

receive and provide annotations at designated moments during the digital simulation including attaching a time stamp to respective ones of the annotations that corresponds to at least a point in time during the digital simulation at which the respective annotations are received or provided, wherein the annotations include particular surgical steps to avoid the at least one adverse event;

allow a surgeon to perform an image-guided surgical procedure based on the selected surgical path to treat the organ having the identified condition on the subject patient; and presenting the annotations that include particular surgical steps to avoid the at least one adverse event at designated times during the image-guided surgical procedure.

4. The computer-readable medium of claim 3, wherein the annotations comprise at least one of audio files, video files, and text files.

5. A non-transitory computer-readable medium that stores executable components, implemented for image guided surgical-planning and procedures, comprising:

a component to compile data regarding study patients who have undergone surgical procedures for surgery on an organ of a subject patient having an identified condition;

a component to produce a three-dimensional (3D) model of an affected area of the subject patient's body and 3D models of the study patients;

a component to determine similarity scores based on a similarity of the 3D model of the affected area of the subject patient and the 3D models of the study patients;

a component to filter data of the study patients based on a threshold value of the similarity scores to produce a set of comparative patients;

a component to determine a plurality of surgical paths to the organ to address the identified condition for the surgical procedures;

a component to determine adverse event scores for each of the plurality of surgical paths based on a relationship between attributes determined for the set of comparative patients and correlation coefficients for at least one adverse event that occur during the surgical procedures for the set of comparative patients and occurrences of the at least one adverse event;

a component to determine a ranking of the plurality of surgical paths for the subject patient based on the determined adverse event scores;

a component to rearrange the plurality of surgical paths for the subject patient based on the rankings;

a component to select a surgical path to treat the identified condition that is to be performed on the organ of the subject patient based on the ranking of the plurality of surgical paths;

a component to produce a digital simulation of the selected surgical path to the organ for the subject patient, wherein the digital simulation comprises at least one of a virtual reality (VR) simulation and an augmented reality (AR) simulation, wherein during the digital simulation, data pertaining to at least one adverse event is displayed during the simulated selected surgical path;

a component to receive and provide annotations at designated moments during the digital simulation including attaching a time stamp to respective ones of the annotations that corresponds to at least a point in time during the digital simulation at which the respective annotations are received or provided, wherein the annotations include particular surgical steps to avoid the at least one adverse event;

a component to allow the selection of an image-guided surgical procedure based on the selected surgical path by a surgeon to perform on the organ of the subject patient to treat the identified condition; and a component to present the annotations that include particular surgical steps to avoid the at least one adverse event at designated times during the surgical procedure.

6. The method of claim 1, further comprising:
- simulating a display of one or more virtual organs to be operated upon via the VR surgical practice equipment; and
- simulating at least one of moving, cutting, suturing, or coagulating for the one or more virtual organs via the VR surgical practice equipment.

7. The method of claim 1, further comprising:
- obtaining the annotations from the digital simulation on the VR surgical practice equipment;
- identifying a position of the patient relative to an augmented reality (AR) display; and
- presenting the annotations from the digital simulation on the VR surgical practice equipment.

8. The method of claim 1, further comprising:
- managing images provided during the image-guided surgical procedure by enabling the surgeon to include or exclude image segments from the annotations.

9. The method of claim 1, wherein the adverse event is blood loss and/or drop in blood pressure.

10. The method of claim 3, wherein the adverse event is blood loss and/or drop in blood pressure.

11. The method of claim 5, wherein the adverse event is blood loss and/or drop in blood pressure.

\* \* \* \* \*